(12) United States Patent
Wolf et al.

(10) Patent No.: US 11,857,494 B2
(45) Date of Patent: Jan. 2, 2024

(54) PERITONEAL DIALYSIS SYSTEM

(71) Applicant: Fresenius Medical Care Deutschland GmbH, Bad Homburg (DE)

(72) Inventors: Klaus Wolf, Muedesheim (DE); Manuel Hassler, Frankfurt am Main (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 826 days.

(21) Appl. No.: 16/613,441

(22) PCT Filed: May 16, 2018

(86) PCT No.: PCT/EP2018/062716
§ 371 (c)(1),
(2) Date: Nov. 14, 2019

(87) PCT Pub. No.: WO2018/210926
PCT Pub. Date: Nov. 22, 2018

(65) Prior Publication Data
US 2020/0179224 A1    Jun. 11, 2020

(30) Foreign Application Priority Data
May 16, 2017  (DE) ............. 10 2017 110 573.5

(51) Int. Cl.
*A61J 1/16* (2023.01)
*A61M 1/28* (2006.01)

(52) U.S. Cl.
CPC .......... *A61J 1/16* (2013.01); *A61M 1/28* (2013.01); *A61M 2209/06* (2013.01)

(58) Field of Classification Search
CPC .......... A61J 1/16; A61M 1/28; A61M 2209/06
USPC .................................... 604/408, 4.01, 6.01
See application file for complete search history.

(56) References Cited

U.S. PATENT DOCUMENTS

| | | | |
|---|---|---|---|
| 4,585,436 A * | 4/1986 | Davis | A61M 1/1643 604/83 |
| 4,589,557 A * | 5/1986 | Bollmann | F16M 13/02 248/222.51 |
| 5,170,817 A * | 12/1992 | Sunderland | A61M 5/1413 137/343 |

(Continued)

FOREIGN PATENT DOCUMENTS

| | | |
|---|---|---|
| DE | 10 023 600 | 2/2002 |
| EP | 0 950 422 | 10/1999 |

*Primary Examiner* — Jacob K Ackun
(74) *Attorney, Agent, or Firm* — Jacobson Holman PLLC

(57) ABSTRACT

The present invention relates to a peritoneal dialysis system comprising at least one peritoneal dialysis machine and at least one organization system that is configured to carry the peritoneal dialysis machine and/or one or more functional elements that are connected to the peritoneal dialysis machine or are connectable thereto, wherein the organization system can be folded for purposes of transport or storage and can be set up, starting from the folded state, into its functional state for the purpose of carrying out the peritoneal dialysis treatment, with the organization system having one or more carrier elements for carrying the peritoneal dialysis machine itself and/or the functional element or elements at least in its set up functional state.

8 Claims, 1 Drawing Sheet

(56) References Cited

U.S. PATENT DOCUMENTS

| | | | | |
|---|---|---|---|---|
| 5,375,717 | A | * | 12/1994 | Roshdy ............... B65D 81/056 206/464 |
| 5,782,796 | A | | 7/1998 | Din et al. |
| 6,284,139 | B1 | | 9/2001 | Piccirillo |
| 6,632,189 | B1 | * | 10/2003 | Fallen .................. A61M 1/367 604/4.01 |
| 2003/0218623 | A1 | * | 11/2003 | Krensky ............... A61M 1/166 604/29 |
| 2003/0220605 | A1 | * | 11/2003 | Bowman, Jr. ......... A61M 5/145 264/109 |
| 2008/0093246 | A1 | * | 4/2008 | Duchamp ............. B65D 85/38 210/646 |
| 2008/0200867 | A1 | * | 8/2008 | Bedingfield ......... H05K 9/0094 604/29 |
| 2008/0277219 | A1 | | 11/2008 | McCarthy |
| 2016/0074568 | A1 | * | 3/2016 | Giordano ........... A61M 1/3661 210/195.2 |
| 2018/0221560 | A1 | * | 8/2018 | Niemetz .............. A61M 60/37 |
| 2019/0022299 | A1 | * | 1/2019 | Schrörs .............. A61M 1/3653 |
| 2020/0016311 | A1 | * | 1/2020 | Giordano ........... A61M 1/3661 |

\* cited by examiner

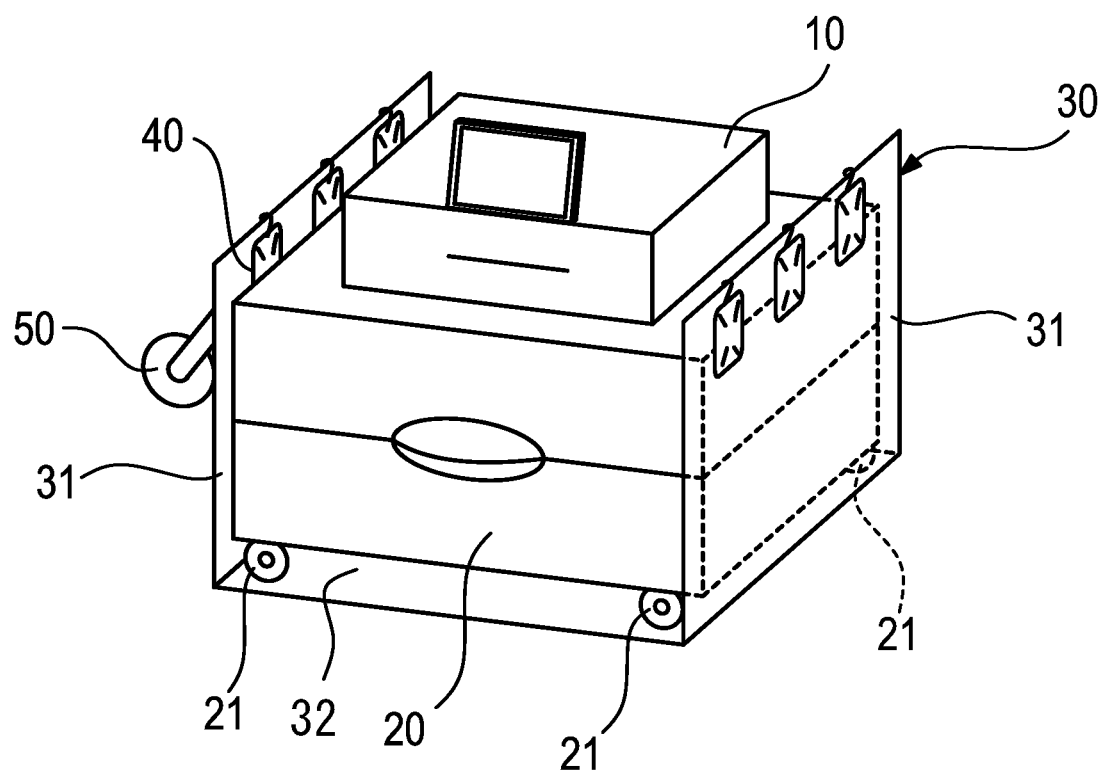

PERITONEAL DIALYSIS SYSTEM

The present invention relates to a peritoneal dialysis system comprising at least one peritoneal dialysis machine as well as at least one organization system that is configured to carry the peritoneal dialysis machine and/or one or more functional elements that are connected to the peritoneal dialysis machine or are connectable thereto.

Peritoneal dialysis is carried out by patients at a typical treatment site which does not necessarily have to be a practice or clinic. The peritoneal dialysis frequently takes place at home or in the home bedroom. The patients typically use a so-called porter, i.e. an organization system that serves to organize the peritoneal dialysis machine, the required solution bags, the drainage system, and the patient connection and to assist it as much as possible.

The present invention is not restricted to a specific kind of PD treatment and not to a specific PD machine. It can, for example, be an APD machine in which all the steps or a plurality of steps such as the opening and closing of clamps and the starting and stopping of pumps takes place in an automated manner.

It can be a gravimetric unit in which the flow of the solutions is effected by gravity and/or a unit having one or more pumps that have the purpose of conveying the solution.

If the patients are on a trip, such as on vacation, this porter is frequently not available or takes up a great deal of space when traveling so that a trip becomes fully impossible or can at best only take place with a lot more trouble.

It is thus the underlying object of the present invention to further develop a peritoneal dialysis system of the initially named kind such that a good preparation of the treatment or a good organization of the peritoneal dialysis machine, of the consumable materials, and of the patient connection and disconnection is also possible for the peritoneal dialysis patient on trips.

This object is achieved by the invention of a peritoneal dialysis system comprising at least one peritoneal dialysis machine and at least one organization system that is configured to carry the peritoneal dialysis machine and/or one or more functional elements that are connected to the peritoneal dialysis machine or are connectable thereto, characterized in that the organization system can be folded for purposes of transport or storage and can be set up, starting from the folded state, into its functional state for the purpose of carrying out the peritoneal dialysis treatment, with the organization system having one or more carrier elements for carrying the peritoneal dialysis machine itself and/or the functional element or elements.

Provision is accordingly made that the organization system can be folded for transport or storage purposes and can be set up starting from the folded state into its functional state for the purpose of carrying out the peritoneal dialysis treatment, wherein the organization system has, at least in its set up functional state, one or more carrier elements for carrying the peritoneal dialysis machine itself and/or the functional element or elements such as solution bags, etc.

It is the underlying idea of the present invention to develop the organization system such that it can be folded by the patient and can thus easily be taken along on trips. The patient can unfold, open, etc. the folded organization system again on site so that it is available for the upcoming peritoneal dialysis treatment.

The peritoneal dialysis machine is preferably an APD machine, i.e. a machine that has one or more pumps for conveying the fresh and/or used dialyzate. The invention is, however, not restricted to such peritoneal dialysis machines.

The organization system is preferably light so that it is easy to transport. It can, for example, be foldable or closable such that its outer dimensions or its volume is reduced with respect to the set up functional condition in which it is available for the peritoneal dialysis.

The functional element or elements that is/are carried, fixed, held, etc. by the organization system can be any desired element that the patient requires as part of the peritoneal dialysis treatment.

A non-exclusive list, for example, includes solution bags that contain the fresh peritoneal dialysis solution, drainage bags for receiving the used dialyzate, hoses or hose system for conducting the dialyzate, valves for controlling the dialyzate flow, organizers for receiving connectors of the hose kit having further lines and the patient connection, connectors, etc.

The organization system can, for example, comprise one or more integrated hooks or other holding means for holding the solution bags. Alternatively or additionally, the organization system can comprise one or more integrated receivers or other holding means for the organizer and/or for the patient connector.

It is conceivable that the organization system is self-supporting or is carried or stabilized by the transport case in which the peritoneal dialysis machine is transported and/or by the peritoneal dialysis machine.

The organization system preferably comprises a lightweight, foldable construction that takes up little room in the folded state and in particular has room in a transport case in which the peritoneal dialysis machine is transported.

The organization system can be configured as a simple rack or can have one or more walls that serves as a cover panel of the peritoneal dialysis machine and/or of its transport case.

The organization system can have at least one placement area on which the peritoneal dialysis machine can be placed. The placement area can be vertically adjustable so that the machine can be simply positioned at the desired height relative to the patient.

It is also conceivable that the peritoneal dialysis system has a transport case in which the peritoneal dialysis machine is located during transport, wherein a surface of the transport case serves as a placement area for the peritoneal dialysis machine on its use.

In a preferred embodiment of the invention, the organization system has one or more receivers or suspensions for the solution bag or bags containing the fresh dialysis solution that are required as part of the peritoneal dialysis treatment.

The organization system can comprise one or more receivers or suspensions for the drainage bag or bags into which the used dialysis solution is drained. Provision is, however, preferably made that the drainage bag or bags are received in the transport case in which the peritoneal dialysis machine is transported.

It is furthermore conceivable that the organization system has rollers by means of which the organization system is travelable so that it can be traveled into the most favorable position for the treatment.

Alternatively or additionally, the transport case in which the peritoneal dialysis machine is located during the transport can also have rollers that are preferably integrated in the case. If the transport case serves as a table for the peritoneal dialysis machine, this is particularly sensible since the peritoneal dialysis machine located on the transport case can thus easily be traveled into the desired position.

To be able in particular to provide an ideal height for solution bags and drainage bags, provision can furthermore be made that the organization system is designed overall or at least partially as vertically adjustable.

The organization system is preferably configured such that it has at least one placement area above the peritoneal dialysis machine in its functional state i.e. in the non-folded state. Accessories can, for example, be placed thereon. The organization system can also have a surface that is preferably likewise arranged above the peritoneal dialysis machine and that e.g. serves to open a double-chamber bag.

The organization system can be integrated at or in the transport case or the organization system can be configured as a unit separate from the transport case.

The transport case can be configured such that one or more bars having holders and/or other receivers or holders for one or more functional elements, in particular for solution bags, are arranged at the transport case. The transport case itself can thus be used, alternatively or additionally to the organization system, to hold or carry solution bags, organizers, etc.

In a further preferred embodiment of the invention, the transport case has at least one leadthrough for at least one hose and at least one receiver for at least one functional element, in particular for a drainage bag. The drainage thus takes place in the case or in the drainage bag or bags located therein.

It is pointed out at this point that the term "bag" is representative for any desired container in which a dialysis solution can be received. It can be, but therefore does not have to be, a container having flexible walls; the use of a box with rigid walls is also covered by the invention and by the term "bag", for example.

Provision can generally be provided that a slanted insert is arranged in the case and a hose leadthrough for leading through a hose from the drainage bag located on the slope to the peritoneal dialysis machine. Alternatively or additionally, solution bags having fresh dialysis solution can be arranged on the slope. They can then be conducted to the patient by means of the hose guided through the hose leadthrough. The slope is preferably designed such that the bag having the fresh dialysis solution runs out completely, i.e. such that the fresh dialysis solution fully reaches the patient.

The dialysis solution bag can in particular also be accommodated in the case with machines having pump systems. The slanted base ensures a complete running out of the solution bag.

The organization system can partially or completely surround the peritoneal dialysis machine and/or the transport case as a cover panel in its functional state, i.e. in the non-folded state.

The total peritoneal dialysis system or at least a part thereof can thus be covered or visually integrated into the treatment room.

It is conceivable that the organization system is available in different materials and/or with different surfaces such that it can be adapted to the onsite circumstances and desires of the patient.

The organization system preferably covers the peritoneal dialysis machine and the transport case so that the peritoneal dialysis machine is not perceived as a medical device at home or in the treatment room during and outside the treatment.

The organization system can have reception regions in which disposable, i.e. disposable articles, such as the hose system, disinfection caps, disinfectants, etc. can be received.

The present invention furthermore relates to a peritoneal dialysis system comprising at least one peritoneal dialysis machine as well as at least one transport case in which the peritoneal dialysis system can be received, and at least one organization system that is configured to carry the peritoneal dialysis machine and/or one or more functional elements that are connected to the peritoneal dialysis machine or are connectable thereto, with the organization system being at least partially formed by the transport case and/or being arranged thereat.

It is thus, for example, conceivable that a bar is provided that can be pushed into the transport case, that is preferably telescopic and at which one or more functional elements such as solution bags can be suspended. It is also possible that the transport case has an extensible grip that serves as a bag holder.

The transport case can additionally have an integrated receiver for the organizer. It can, for example, be folded out so that it is not obstructive during transport. This can apply accordingly to further holders of the case.

The present invention comprises the peritoneal dialysis system with and also without the named functional elements such as solution bags, organizer, drainage bags, hose system, etc.

The transport case can be placed onto the bottom plate of the organization system. This arrangement may possibly give the organization system additional stability.

The present invention furthermore relates to a method of preparing a peritoneal dialysis treatment, wherein a peritoneal dialysis system in accordance with the instant invention is used for the preparation. The method thus does not relate to the treatment as such, but rather to its preparation.

This can e.g. comprise the setup of the organization system or the provision of the transport case, the equipping with the required functional elements and the correct positioning of the peritoneal dialysis machine.

The patient preferably removes the peritoneal dialysis machine and the organization system from the transport case, sets up the organization system, places the peritoneal dialysis machine on the transport case and equips the organization system and/or the transport case with solution bags, drainage bags, connects the hose system, etc.

Further details and advantages of the invention will be explained in more detail with reference to an embodiment shown in the drawing.

BRIEF DESCRIPTION OF THE DRAWINGS

FIG. 1 schematically shows the peritoneal dialysis system in accordance with the invention in the set up state.

Reference numeral 10 marks an APD peritoneal dialysis machine that is supported on the transport case 20. The transport case for the peritoneal dialysis machine in this case serves as a table for the peritoneal dialysis machine.

The foldable organization system that can be stowed in the transport case 20 together with the peritoneal dialysis machine in the folded together state is marked by the reference numeral 30.

As can be seen from FIG. 1, the organization system 30 extends on two oppositely disposed sides of the transport case 20 and of the peritoneal dialysis machine 10 in the form of substantially perpendicular walls 31 or rack parts. The organization system can furthermore have a base plate to stabilize walls.

The walls/rack parts have a height that exceeds that of the lying transport case 20 and that extends up to and into the region of the peritoneal dialysis machine 10. The transport case 20 has an upper side on which the peritoneal dialysis machine stands and a lower side provided with rollers 21 resting on placement area 32 of organization system 30. The transport case 20 can thus be moved together with the peritoneal dialysis machine 10 and the organization system 30 so that an ideal position for the patient can be achieved.

Holding means such as hooks, etc. at which solution bags 40 are suspended that contain the fresh dialysis solution to be administered are located at the upper end of the walls 31.

They are connected to the peritoneal dialysis machine via a hose system, not shown. The peritoneal dialysis machine conveys the fresh dialysis solution through the hose system to the patient catheter, not shown, through which it enters into the abdomen of the patient. After a dwell time, the dialysis solution is pumped out again and is emptied into a drainage bag via the patient catheter and a hose system, not shown, that extends through an opening in the case 20. Said drainage bag is located in the closed case 20 on which the peritoneal dialysis machine stands.

Reference numeral 50 marks an organizer located at the organization system.

The advantages of the present invention preferably comprise the organization system being light, portable, space-saving and compact and the patient not having to get used to something new when he is on a trip. It is generally also conceivable that this is the preferred option of the home patient, for example with tight space conditions in the domestic environment such as in the bedroom.

On trips and also at home, the usual procedures can be maintained, which results in a reduction of possible errors in the application or treatment that could possibly result in peritonitis.

Solution bags, the drainage system, and the organizer as well as the PD or APD machine per se can preferably in particular be positioned at the desired points and at the desired height by the organization system and/or by the transport case such that a smooth and trouble-free treatment during the night is inter alia ensured.

The invention claimed is:

1. A peritoneal dialysis system comprising
   at least one peritoneal dialysis machine,
   a transport case for storing or transporting the dialysis machine or supporting the dialysis machine when in use, and
   at least one foldable organization system formed by a rack or frame, having a placement area disposed between two opposing walls and configured to carry the peritoneal dialysis machine supported on the transport case and/or one or more peritoneal dialysis functional elements that are connected to the peritoneal dialysis machine or are connectable thereto, characterized in that the organization system is folded for purposes of transport or storage in the transport case and can be set up, starting from the folded state, into its functional state for the purpose of carrying out the peritoneal dialysis treatment, with the organization system having one or more carrier elements for carrying the functional element or elements.

2. A peritoneal dialysis system in accordance with claim 1, characterized in that the peritoneal dialysis functional element elements is/are one or more of the following elements: solution bags, drainage bags.

3. A peritoneal dialysis system in accordance with claim 1, characterized in that the transport case has rollers by means of which the organization system is travelable.

4. A peritoneal dialysis system in accordance with claim 1, characterized in that the transport case can receive the peritoneal dialysis machine; and in that the organization system is designed as a unit separate from the transport case.

5. A peritoneal dialysis system in accordance with claim 1, characterized in that the transport case can receive the peritoneal dialysis machine.

6. A peritoneal dialysis system in accordance with claim 1, characterized in that the transport case can receive the peritoneal dialysis machine, a drainage bag, and/or a solution bag.

7. The peritoneal dialysis system in accordance with claim 1, characterized in that the organization system partially or completely surrounds the peritoneal dialysis machine in its functional state.

8. A peritoneal dialysis system comprising at least one peritoneal dialysis machine as well as at least one transport case in which the peritoneal dialysis system can be received, and at least one foldable organization system formed by a rack or frame and having a placement area configured to carry the peritoneal dialysis machine supported on the transport case and/or one or more functional elements that are connected to the peritoneal dialysis machine or are connectable thereto, characterized in that the organization system is arranged at the transport case.

* * * * *